US011384044B2

(12) United States Patent
Suzuki et al.

(10) Patent No.: US 11,384,044 B2
(45) Date of Patent: Jul. 12, 2022

(54) METHOD FOR INTRODUCING SUBSTITUENT INTO α,β-UNSATURATED KETONE AND METHOD FOR SYNTHESIZING PROSTAGLANDIN USING THE SAME

(71) Applicant: NATIONAL CENTER FOR GERIATRICS AND GERONTOLOGY, Obu (JP)

(72) Inventors: Masaaki Suzuki, Obu (JP); Hiroko Koyama, Gifu (JP)

(73) Assignee: NATIONAL CENTER FOR GERIATRICS AND GERONTOLOGY, Aichi (JP)

( * ) Notice: Subject to any disclaimer, the term of this patent is extended or adjusted under 35 U.S.C. 154(b) by 238 days.

(21) Appl. No.: 16/635,736

(22) PCT Filed: May 29, 2018

(86) PCT No.: PCT/JP2018/020527
§ 371 (c)(1),
(2) Date: Jan. 31, 2020

(87) PCT Pub. No.: WO2019/026402
PCT Pub. Date: Feb. 7, 2019

(65) Prior Publication Data
US 2021/0355061 A1    Nov. 18, 2021

(30) Foreign Application Priority Data
Aug. 3, 2017   (JP) .............................. JP2017-150745

(51) Int. Cl.
*C07C 51/09*  (2006.01)
*C07C 405/00* (2006.01)
*C07F 3/06*   (2006.01)
*C07F 7/22*   (2006.01)

(52) U.S. Cl.
CPC ............ *C07C 51/09* (2013.01); *C07C 405/00* (2013.01); *C07C 405/0025* (2013.01); *C07F 3/06* (2013.01); *C07F 7/2208* (2013.01)

(58) Field of Classification Search
CPC . C07C 51/09; C07C 405/00; C07C 405/0016; C07C 405/0025; C07F 3/06; C07F 7/2208
See application file for complete search history.

(56) References Cited

PUBLICATIONS

Morita et al., An organozinc acid in alkylation and acylation of lithium enolates, J. Org. Chem., vol. 54, No. 8, pp. 1785-1787 (Year: 1989).*
Suzuki et al., Three-component coupling synthesis of prostaglandins, A simplified, general procedure, Tetrahedron, vol. 46, No. 13/14, pp. 4809-4726 (Year: 1990).*
Gooding, et al., Triply convergent synthesis of 15-(phenoxymethyl) and 4,5-allenyl prostaglandins. Preparation of an individual isomer of enprostil, J. Org. Chem., vol. 58, pp. 3681-3686 (Year: 1993).*
Chen et al., Expeditious entry to the chamigrane endoperoxide family of natural products, Organic Letters, vol. 17, pp. 592-595 (Year: 2015).*
Chen et al., "Expeditious Entryto the Chamigrane Endoperoxide Family of Natural Products," Organic Letters (2015), vol. 17, pp. 592-595.
Gooding et al., "Triply Convergent Synthesis of 15(Phenoxymethyl) and 4,5-Allenyl Prostaglandins: Preparation of an Individual Isomer of Enprostil," J. Org. Chem, (1993), vol. 58, pp. 3681-3686.
Holec et al., "Chemoenzymatic Synthesis towards the Active Agent Travoprost," ChemCatChem (2015), vol. 7, pp. 3125-3130.
International Preliminary Report on Patentability and Written Opinion dated Feb. 13, 2020, in PCT/JP2018/020527 (Forms PCT/IB/326, PCT/IB/373, and PCTISA/237).
International Search Report dated Aug. 28, 2018, in PCT/JP2018/020527.
Lipshutz, B. H. and M. R. Wood, "A Practical, General Three-Component Coupling Approach to Prostaglandin and Non-Prostaglandin-Related Skeleta," J. Am. Chem. Soc. (1994), vol. 116, pp. 11689-11702.
Morita et al., "An Organozinc Aid in Alkylation and Acetylation of Lithium Enolates," J. Org. Chem. (1989), vol. 54, No. 8, pp. 1785-1787.
Suzuki et al., "(15R)-16-m-Tolyl-17,18,19,20-tetranorisocarbacyclin: A Stable Ligand with High Binding Affinity and Selectivity for Prostacyclin Receptor in the Central Nervous System," Angew. Chem., Int. Ed. Eng. (1996), vol. 35, 334-336.
Suzuki et al., "15-Deoxy-16(m-tolyl)-17,18,19,20-tetranorisocarbacyclin: a simple TIC derivative with potent anti-apoptotic activity for neuronal cells," Chem. Commun. (1999), pp. 307-308.
Suzuki et al., "An Extremely Short Way to Prostaglandins," J. Am. Chem. Soc. (1985), vol. 107, pp. 3348-3349.

(Continued)

*Primary Examiner* — Yate' K Cutliff
(74) *Attorney, Agent, or Firm* — Birch, Stewart, Kolasch & Birch, LLP

(57) ABSTRACT

The present invention provides a method for introducing substituents into the α-position and the β-position of an α,β-unsaturated ketone, which not only can be used for the synthesis of a prostaglandin by a three-component coupling process, but also enables synthesis of a prostaglandin in a high yield by one-pot operation without requiring the use of a large excess amount of any of the three components required for the synthesis or using a highly toxic heavy metal as a catalyst or a solvent that is highly toxic to living bodies, and a method for synthesizing a prostaglandin using the same technical means.
The method for introducing substituents into an α,β-unsaturated ketone according to the present invention is a method for introducing substituents into the carbon at the α-position and the carbon at the β-position of an α,β-unsaturated ketone, including: a first step of mixing alkyllithium and trialkylalkenyl tin in which tin atom binds to the vinyl position of the alkenyl group; a second step of mixing the mixture of the first step and dialkylzinc; a third step of mixing the mixture of the second step and an α,β-unsaturated ketone; and a fourth step of mixing the mixture of the third step and a trifluoromethanesulfonate compound.

3 Claims, No Drawings

(56) References Cited

PUBLICATIONS

Suzuki et al., "Rapid methylation on carbon frameworks leading to the synthesis of a PET tracer capable of imaging a novel CNS-type prostacyclin receptor in living human brain," Trends in Analytical Chemistry (2004), vol. 23, No. 8, pp. 595-607.

Suzuki et al., "The Three-Component Coupling Synthesis of Prostaglandins," J. Am. Chem. Soc. (1988), vol. 110, pp. 4718-4726.

Suzuki et al., "Three-Component Coupling Synthesis of Prostaglandins. A Simplified, General Procedure," Tetrahedron (1990), vol. 46, Nos. 13/14, pp. 4809-4822.

* cited by examiner

METHOD FOR INTRODUCING SUBSTITUENT INTO α,β-UNSATURATED KETONE AND METHOD FOR SYNTHESIZING PROSTAGLANDIN USING THE SAME

TECHNICAL FIELD

The present invention relates to a method capable of introducing arbitrary substituents into the carbon at the α-position and the carbon at the β-position of an α,β-unsaturated ketone in one pot, and a method for synthesizing a prostaglandin using the same technical means.

BACKGROUND ART

Reactions of an α,β-unsaturated ketone characterized by conjugated double bond substituted with an electron-withdrawing carbonyl group are vulnerable to attack to the β-position by a soft nucleophile (for example, a stable carbanion, alkyllithium, or an organocopper reagent adjusted from a Grignard reagent and a copper salt) (so called, Michael addition), and are highly useful as carbon skeleton formation reactions of various compounds If arbitrary substituents can be introduced into the alkene double bond (i.e., carbon at the α-position and carbon at the β-position) in α,β-unsaturated ketones, various useful compounds can be synthesized. For example, prostaglandins (PGs) have a structure in which an α-chain substituent and an ω-chain substituent are introduced into the α-position and the β-position of 4-hydroxy-2-cyclopenten-1-one, which is a kind of α,β-unsaturated ketones, as shown in the following chemical structural formula. Therefore, various prostaglandins can be synthesized if arbitrary substituents can be introduced into the α-position and the β-position of α,β-unsaturated ketones.

[Chemical Formula 1]

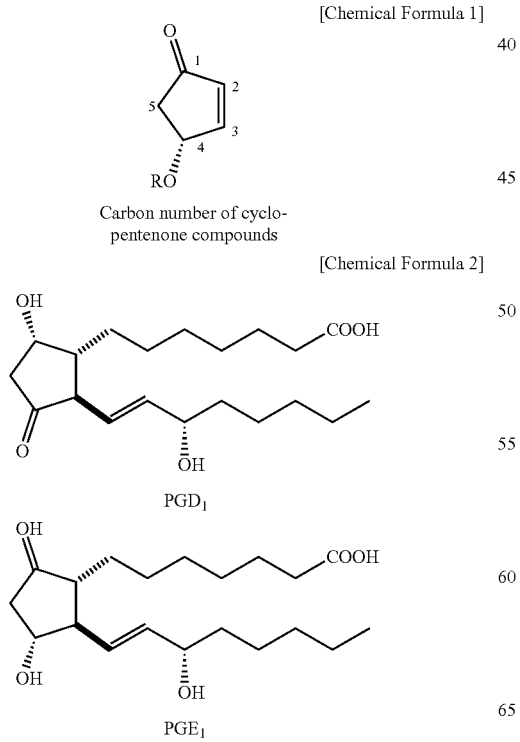

Carbon number of cyclopentenone compounds

[Chemical Formula 2]

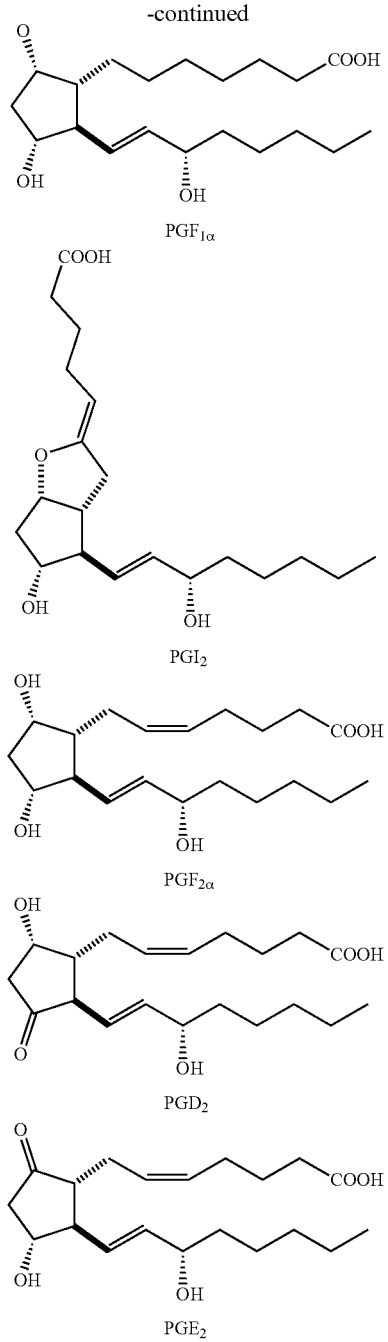

A prostaglandin (PG) is an ultra-trace bioactive substance that functions to maintain the homeostasis of living bodies. In addition to actions of the peripheral system, it also exhibits actions of the central nervous system (CNS) such as sleep, fever, pain, and neuroprotection, and has attracted great attention. However, the content of PGs in a natural product is extremely small, and it is difficult to collect them from a natural product. For this reason, since Corey reported a route for the synthesis of a natural PG via Corey lactone in 1969, many studies on synthesis have been conducted.

Among those studies on synthesis, the "three-component coupling process", which was developed by the present inventors for the first time in the world, of coupling the α-side chain and ω-side chain sites to the 5-membered ring site of a cyclopentenone compound in one pot, leading to construct all the carbon skeletons of PG at once is an ideal synthesis method that can dramatically reduce the number of steps, and is called the best pivotal reaction for synthesis of PG (Non-Patent Literatures 1 and 2).

[Chemical Formula 3]

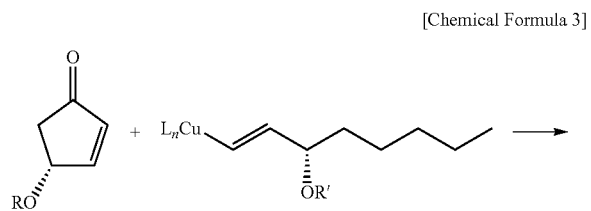

In the three-component coupling process, a 1,4-addition reaction between an organocopper complex having an w-side chain structure and 4-hydroxy-2-cyclopenten-1-one is first performed, as shown in the above chemical formula. Without taking out the product, the reaction of the metal enolate produced in situ with a halogen compound having an α-side chain structure (used in an excessive amount) is continuously performed in the presence of a chlorinated organotin compound and hexamethylphosphoric triamide (HMPA) in THF in the same reaction vessel. According to this three-component coupling process, natural PGs can be synthesized in a short route, and further, the synthesis of isocarbacyclin, which is a chemically stable artificial PG, has been achieved.

In addition, as an improved method of this three-component coupling process, there has been developed a method that uses an organozinc ate complex instead of an organocopper complex, so that neither heavy metals such as copper nor highly toxic organotin chloride compounds are used (Non-Patent Literatures 3 and 4).

Furthermore, this method has been used to create 15R-TIC (an $IP_2$ receptor ligand specifically expressed in the brain), and brain PET research on novel PGs has also been pioneered (Non-Patent Literatures 5 to 7).

CITATIONS LIST

Non-Patent Literature

Non Patent Literature 1: Suzuki, M.; Yanagisawa, A.; Noyori, R. J. Am. Chem. Soc. 1985, 107, 3348-3349.

Non Patent Literature 2: Suzuki, M.; Yanagisawa, A.; Noyori, R. J. Am. Chem. Soc. 1988, 110, 4718-4726.

Non Patent Literature 3: Morita, Y.; Suzuki, M.; Noyori, R. J. Org. Chem. 1989, 54, 1785-1787.

Non Patent Literature 4: Suzuki, M.; Morita, Y.; Koyano, H.; Koga, M.; Noyori, R. Tetrahedron 1990, 46, 4809-4822.

Non Patent Literature 5: Suzuki, M.; Kato, K.; Noyori, R.; Watanabe, Y.; Takechi, H.; Matsumura, K.: Langstrorn, B.; Watanabe, Y. Angew. Chem., Int. Ed. Eng. 1996, 35, 334-336.

Non Patent Literature 6: Suzuki, M.; Kato, K.; Watanabe, Y.; Satoh. T.: Matsumura, K.; Watanabe, Y.; Noyori, R. Chem. Commun. 1999, 307-308.

Non Patent Literature 7: Suzuki, M.; Doi, H.; Hosoya, T.; Langstrom, B.; Watanabe, Y. Trends Anal. Chem, 2004, 23, 595-607.

SUMMARY OF INVENTION

Technical Problems

However, the PG synthesis through the conventional three-component coupling process involves a problem that an excessive amount of an α-side chain halogen compound must be used, and further improvement of the yield has also been demanded. In addition, the conventional three-component coupling process involves problems such as the use of a highly toxic heavy metal as a catalyst and the use of HMPA whose carcinogenic properties are of concern as an additive, and thus is against a social need for green processes on chemical synthesis.

The present invention has been made in view of the above-described conventional problems, and an object of the present invention is to provide a method for introducing substituents into the α-position and the β-position of an α,β-unsaturated ketone, which not only can be used for the synthesis of a prostaglandin by a three-component coupling process, but also enables synthesis of a prostaglandin in a high yield by one-pot operation without requiring the use of large excess amounts of components to be introduced for any of the three component reactions required for the synthesis or using a highly toxic heavy metal as a catalyst or a solvent or an additive that is highly toxic to living bodies, and a method for synthesizing a prostaglandin using the same technical means.

Solutions to Problems

In order to solve the above-mentioned problems, the present inventors have examined the cause of yield reduction in the conventional three-component coupling process. As a result, the present inventors have inferred the cause of the yield reduction as follows: after 1,4-addition to an α,β-unsaturated ketone, proton transfer occurs in the alkylation process of the resulting enolate due to the progress of the hydrogen exchange reaction with the alkylated ketone due to its basicity, with the result that a plurality of byproducts are produced (see the following chemical formula).

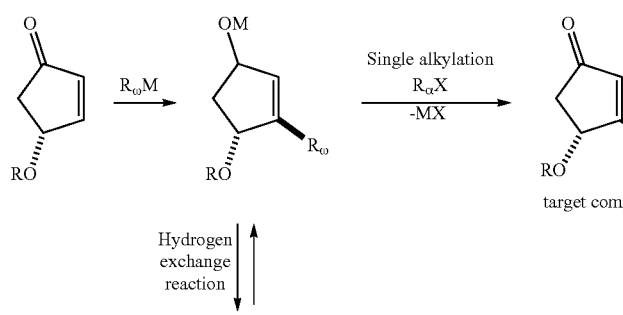

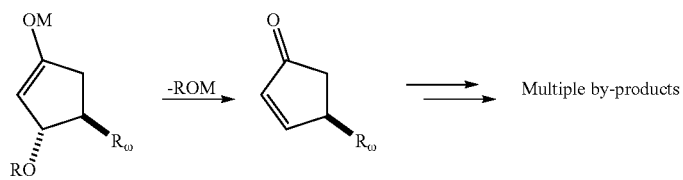

As a method for preventing this hydrogen exchange reaction from occurring in the second-stage reaction, the present inventors have found that it is effective to modify the lithium enolate structure using dialkylzinc. Furthermore, the present inventors have found that the three components, including the zinc ate complex which is responsible for the 1,4-addition reaction, react almost stoichiometrically, by using a trifluoromethanesulfonate compound having an excellent anion leaving group as an electrophile for introducing a substituent into the carbon at the α-position. The above reactions can introduce substituents into the carbon at the α-position and the carbon at the β-position of the α,β-unsaturated ketone in a high yield by one-pot operation without using a highly toxic heavy metal as a catalyst or an additive that is highly toxic to living bodies. For this reason, all the above-indicated conventional problems were solved.

A method for introducing substituents into an α,β-unsaturated ketone according to the present invention is a method for introducing substituents into the carbon at the α-position and the carbon at the β-position of an α,β-unsaturated ketone, including: a first step of mixing alkyllithium and trialkylalkenyl tin in which tin atom binds to the vinyl position of the alkenyl group;
a second step of mixing the mixture of the first step and dialkylzinc;
a third step of mixing the mixture of the second step and an α,β-unsaturated ketone; and
a fourth step of mixing the mixture of the third step and a trifluoromethanesulfonate compound.

A method for synthesizing a prostaglandin according to the present invention is characterized by using the method for introducing substituents into an α,β-unsaturated ketone according to the present invention.

The α,β-unsaturated ketone is a cyclopentenone derivative, the alkenyl group of the trialkylalkenyl tin can be used as a component to be introduced into the ω-side chain of a prostaglandin, and the carbon chain structural part of the trifluoromethanesulfonate compound can be used as a component to be introduced into the α-side chain of the prostaglandin.

[Chemical Formula 4]

DESCRIPTION OF EMBODIMENTS

In the method for introducing substituents into an α,β-unsaturated ketone according to the present invention, as shown in the following chemical formula, alkyllithium and trialkylalkenyl tin in which tin atom binds to the vinyl position of the alkenyl group are first mixed (first step). Thus, the corresponding vinyllithium is produced. Then, the mixture of the first step and dialkylzinc are mixed to produce a zinc-lithium hybrid ate complex (second step). Further, the mixture of the second step and an α,β-unsaturated ketone are mixed (third step). Thus, a vinyl substituent binds to the carbon at the β-position of the vinyl substituent in the α,β-unsaturated ketone (i.e., 1,4-addition occurs). Finally, a substituent binds to the carbon at the α-position of the α,β-unsaturated ketone by mixing the mixture of the third step and a trifluoromethanesulfonate compound (fourth step). At this time, the hydrogen exchange reaction hardly occurs, and almost no byproduct is produced. Thus, different substituents are introduced into the carbon at the α-position and the carbon at the β-position of the α,β-unsaturated ketone.

[Chemical Formula 5]

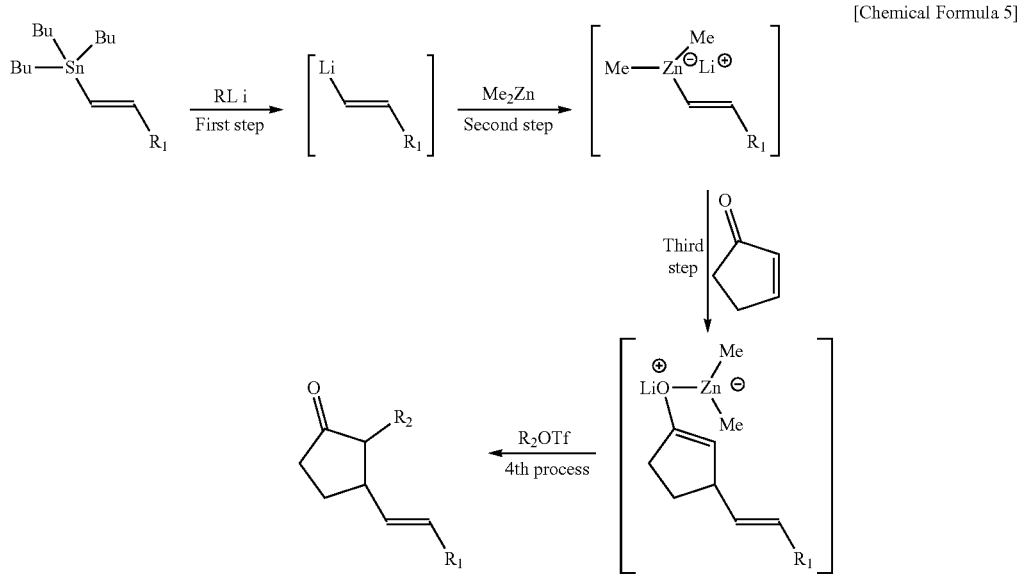

The method for introducing substituents into an α,β-unsaturated ketone according to the present invention can be used for the synthesis of prostaglandins. For example, a 5,6-dehydro-PGE$_2$ derivative (8) can be synthesized by introducing an ω-chain and an α-chain into a cyclopentenone derivative (5) in a manner as shown in the following chemical formula.

[Chemical Formula 6]

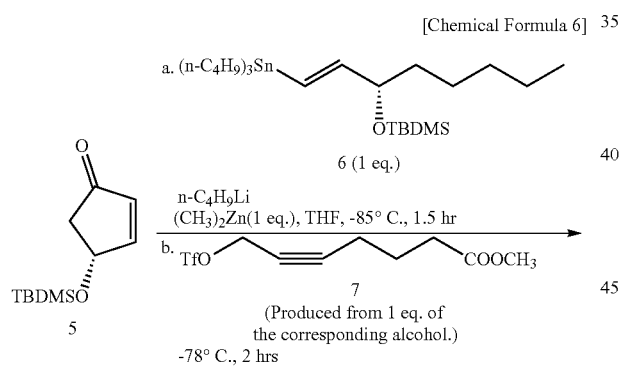

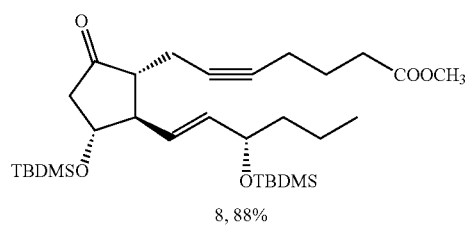

The thus-synthesized 5,6-dehydro PGE2 derivative (8) is a key intermediate for general synthesis methods for natural PGs. An example of the general synthesis method is shown below (as for details, refer to Non-Patent Literatures 1, 2, and 4).

General synthesis of prostaglandins.

[Chemical Formula 7]

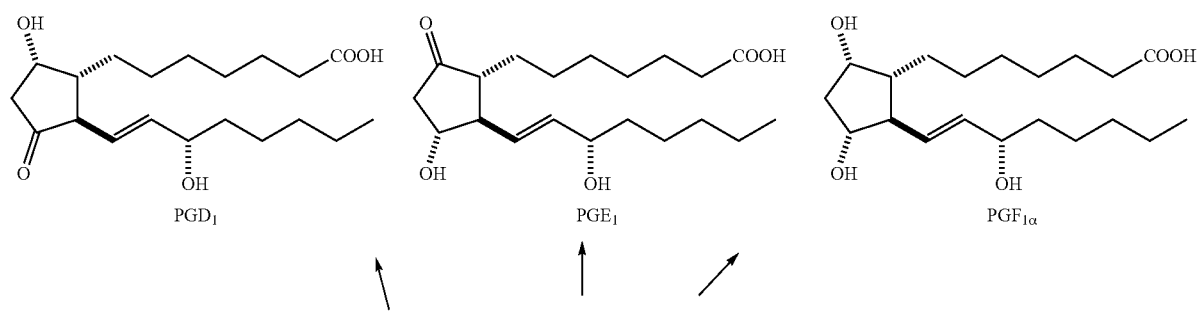

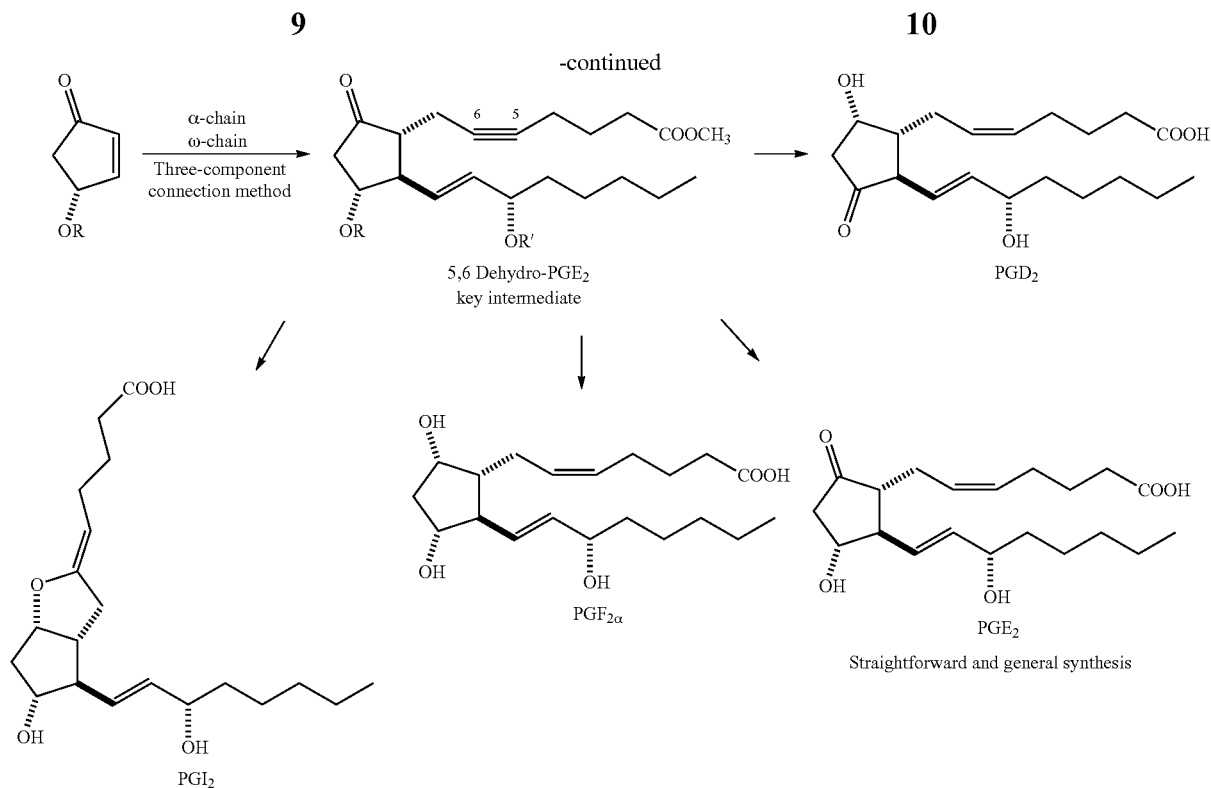
Suzuki, M. et.al, *J.Am.chem.Soc.* (1985,1988); Tetrahedron(1990).
In addition, isocarbacyclin, which is a chemically stable artificial PG, can also be synthesized using the 5,6-dehydro PGE2 derivative (8) as a key intermediate (see the following synthesis route).
Synthesis of isocarbacycline (methyl ester) from key intermediate
[Chemical Formula 8]
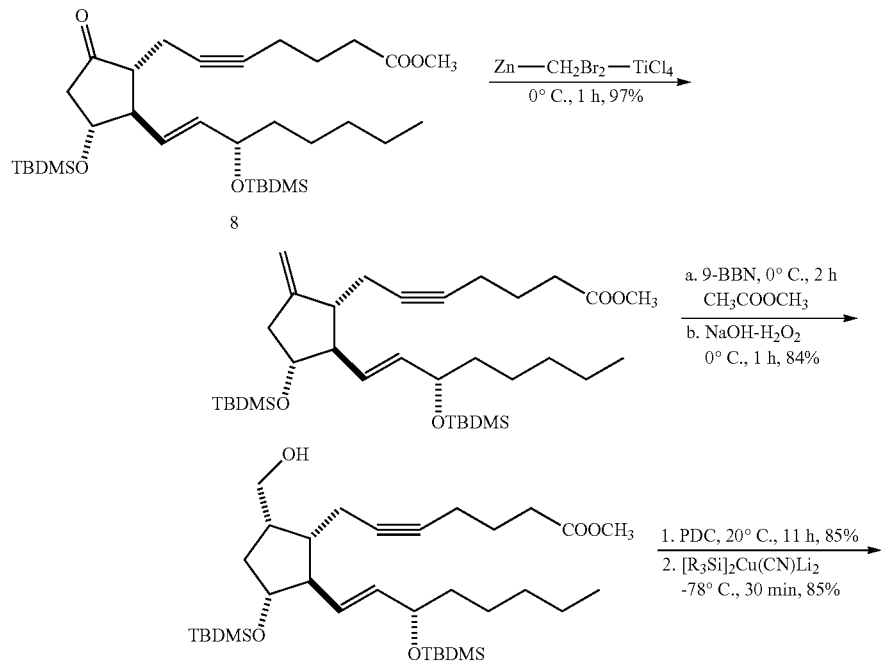

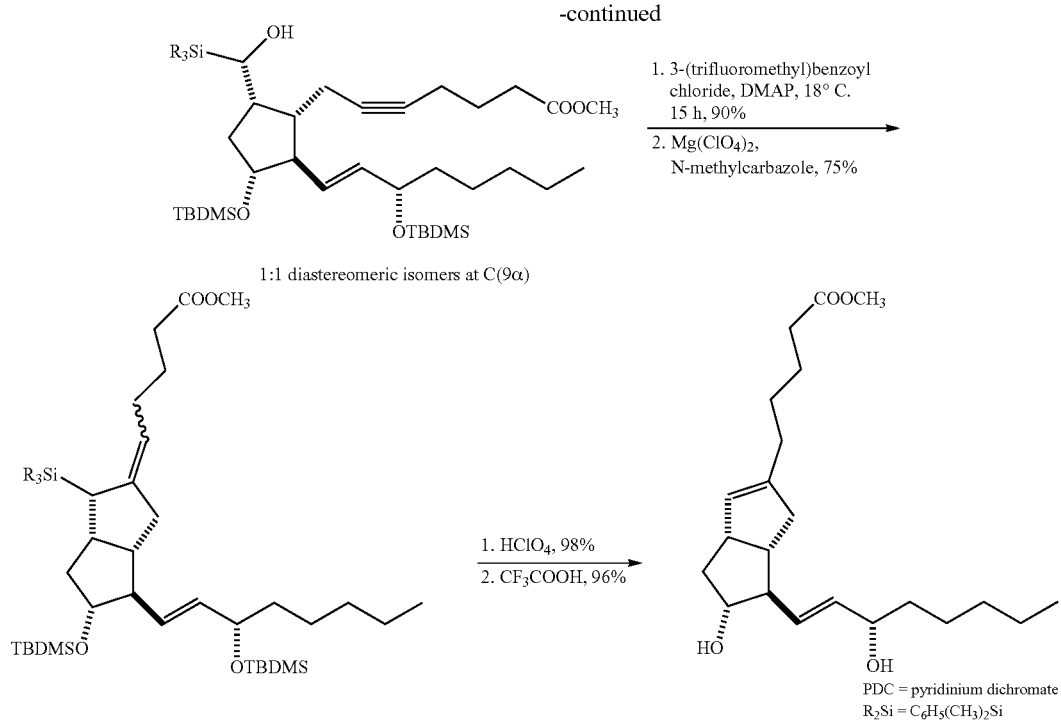

The artificially synthesized isocarbacyclin is a compound having excellent thrombogenesis suppressing activity and, besides, being stable and expected as a pharmaceutical product, particularly an antithrombotic therapeutic agent, which has been found through research to improve the stability of prostacyclin (another name: prostaglandin I2) similarly exhibiting thrombogenesis suppressing activity. Conventionally, this isocarbacyclin has been derived from the previously-described intermediate for the Corey synthesis method (also referred to as Corey lactone), and multi-step synthesis has been inevitable. On the other hand, the method for introducing substituents into an α,β-unsaturated ketone according to the present invention is used, so that the isocarbacyclin can be synthesized in a dramatically short process as shown in the above synthesis route, and that the total yield can also be drastically improved.

Examples in which the present invention was embodied will be described in detail below.

EXAMPLES

Example 1

In Example 1, a prostaglandin compound 8 was synthesized according to the following chemical reaction formula as a compound to be applied to the synthesis of a 5,6-dehydro PGE₂ derivative by a three-component coupling process. This 5,6-dehydro PGE₂ derivative can be a key intermediate for general synthesis methods for natural PGs and for the synthesis of isocarbacyclin as a chemically stable artificial PG. Details are described below.

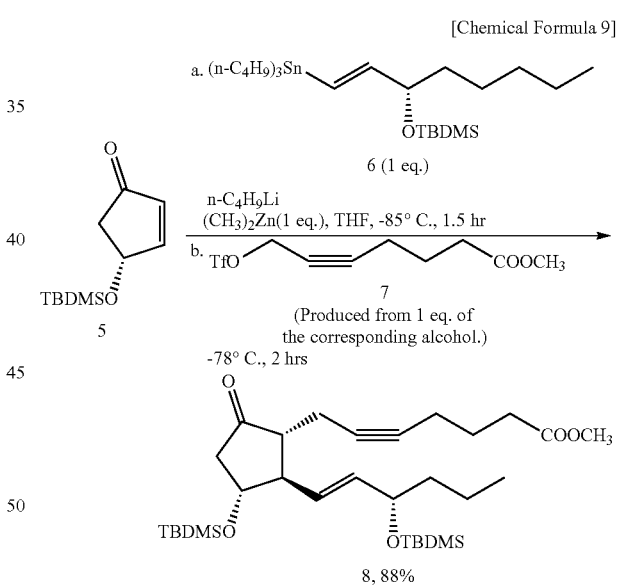

Since the reaction intermediate or reactive species is extremely unstable to water and air, the reaction was carried out under an argon gas stream so that the reaction could be carried out with sufficient cooling under anhydrous conditions. An ampoule equipped with a three-way cock, a corrugated tube for adding enone and dimethylzinc, and a port for adding α-chain and ω-chain was used as a reaction vessel for the three-component coupling process. Each reaction substrate was added to the reaction solution using a stainless steel cannula under argon pressure, and each reaction reagent was added thereto using a gas tight syringe.

A THF solution (1.5 mL) of (S,E)-3-(tert-butyldimethyl-siloxy)-1-(tributylstannyl)-1-octene (6,266 mg, 0.500 mmol) was added to a 50-mL ampoule. After cooling to −85° C. (liquid nitrogen/methanol), n-butyllithium (1.55 M hexane solution, 0.323 mL, 0.500 mmol) was added, and the mixture was stirred at this temperature for 1 hour to adjust vinyllithium. Dimethylzinc (1.0 M hexane solution, 0.50 mL, 0.50 mmol) was added to this mixed solution from the corrugated tube cooled to −85° C. After stirring for 10 minutes, a THF solution (1.5 mL) of (R)-4-(tert-butyldimethylsiloxy)-2-cyclopentenone (5,106 mg, 0.500 mmol) was added over 10 minutes from the corrugated tube cooled to −85° C., and the corrugated tube was rinsed with THF (1.0 mL). While this mixed solution was stirred at this temperature for 1 hour, propargyl triflate (7) was prepared according to the following procedures.

To another two-necked round bottom flask, 2,6-di-tert-butyl-4-methylpyridine (170 mg, 0.83 mmol) was added, and the flask was purged with argon. A diethyl ether solution (1.0 mL) of methyl 7-hydroxy-5-heptynoate (117 mg, 0.600 mmol) was added. The mixed solution was cooled to −21° C. (NaCl/ice), and a diethyl ether solution (1.0 mL) of trifluoromethanesulfonic anhydride (139 μL, 0.83 mmol) was added. The mixture was stirred at this temperature for 15 minutes and then cooled to −78° C. (dry ice/acetone). Hexane (5.0 mL) was added, and the mixture was stirred for 5 minutes. The precipitated salt was filtered through 10 mm-thick celite to collect the filtrate in a 30-mL two-necked round bottom flask cooled to −78° C. under an argon gas. The celite was washed with hexane (8 mL) and diethyl ether (1 mL), and the collected filtrate was cooled to −78° C. until completion of the 1,4-addition reaction.

A hexane-diethyl ether solution of the thus-adjusted triflate 7 was added to the 50-mL ampoule tube containing the 1,4-addition reaction product at −78° C. After stirring this mixed solution for 2 hours, the reaction was stopped with a saturated aqueous $NH_4Cl$ solution. The resulting solution was extracted with diethyl ether (3×5 mL), and the collected organic layer was washed with water (10 mL) and saturated brine (10 mL), and dried over $Na_2SO_4$. After concentration by an evaporator, elution was performed with silica gel column chromatography (eluent:hexane:ethyl acetate 20:1) to obtain the target compound 8 (260.5 mg, 88% yield) as a colorless oily product.

$δ_H$ (400 MHz; $CDCl_3$) −0.02, 0.04, 0.05, and 0.06 (s each, 12H, 4 $CH_3Si$), 0.85 to 0.88 (m, 21H, 2 $(CH_3)_3CSi$ and $CH_3$), 1.19 to 1.51 (m, 8H, 4 $CH_2$), 1.73 to 2.79 (m, 12H, 5 $CH_2$ and 2 CH), 3.65 (s, 3H, $CH_3O$), 4.06 to 4.12 (m, 2H, 2 CHO), 5.48 to 5.66 (m, 2H, vinyl);

$δ_C$ (100 MHz; $CDCl_3$) −4.75, −4.63, −4.58, −4.25, 14.07, 16.72, 18.06, 18.19, 18.23, 22.64, 24.12, 25.08, 25.78 (3C), 25.90 (3C), 31.85, 32.78, 38.48, 47.77, 51.53, 51.81, 52.94, 72.65, 73.07, 77.23, 80.85, 128.01, 136.94, 173.70, 213.96.

Example 2

In Example 2, a prostaglandin compound 10 was synthesized according to the following chemical reaction formula. The prostaglandin compound 10 can be led to (15R)-16-m-tolyl-17,18,19,20-tetranorisocarbacyclin (15R-TIC) by an operation similar to that for the synthesis of isocarbacyclin. This 15R-TIC is a drug discovery compound that binds to the brain prostacyclin ($IP_2$) receptor and exhibits cranial neuroprotective action. The procedures for the synthesis of 15R-TIC are described in detail below.

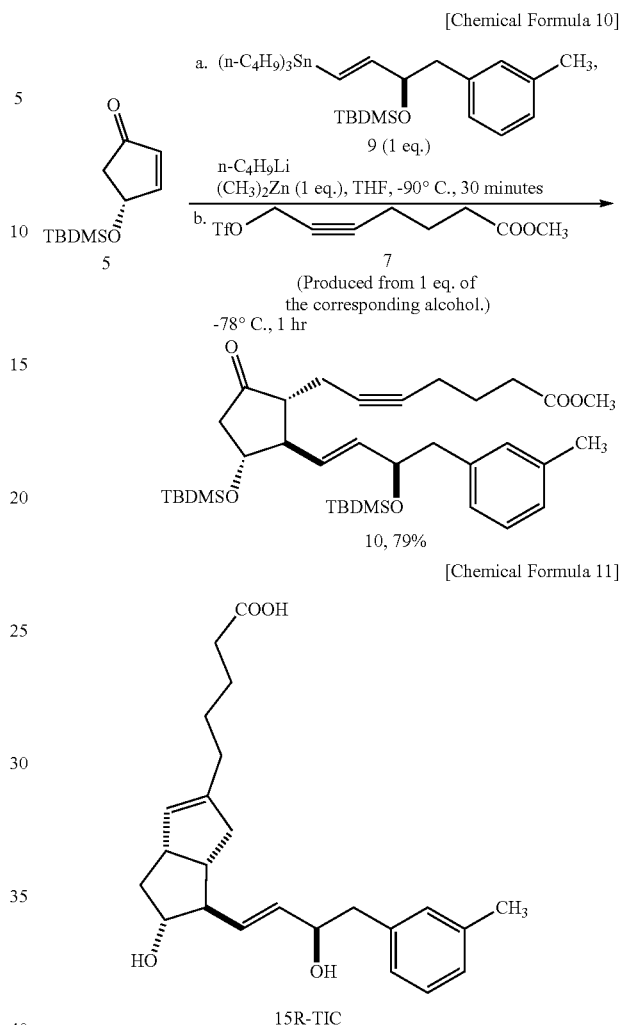

A THF solution (10 mL) of (R,E)-3-[(tert-butylmethylsilyl)oxy]-4-[(3-methy)phenyl]-1-tributylstannyl-1-butene (9) (1.85 g, 3.27 mmol) was added to a 100-mL ampoule. After cooling to −78° C. (dry ice/acetone), n-butyllithium (1.56 M hexane solution, 2.10 mL, 3.27 mmol) was added, and the mixture was stirred at this temperature for 1 hour to adjust vinyllithium. Dimethylzinc (1.0 M hexane solution, 3.3 mL, 3.3 mmol) was added to the mixed solution. After stirring for 10 minutes, a flask with a corrugated tube was cooled to a temperature ranging from −98° C. to −90° C. (liquid nitrogen/methanol), and a THF solution (20 mL) of (R)-4-(tert-butyldimethylsiloxy)-2-cyclopentenone (5) (675 mg, 3.18 mmol) was added over 2 hours using a syringe pump, and the corrugated tube was rinsed with THF (1.0 mL). While this mixed solution was stirred at this temperature for 30 minutes, the corresponding propargyl triflate 7 was obtained from methyl 7-hydroxy-5-heptynoate (745 mg, 4.77 mmol) in a similar manner as in Example 1.

A THF solution (15 mL) of the adjusted propargyl triflate 7 was added to the 100-mL ampoule tube containing the 1,4-addition reaction product at −78° C. After the mixed solution was stirred for 1 hour, the reaction was stopped with a saturated aqueous $NH_4Cl$ solution (10 mL). The resulting solution was extracted with diethyl ether (3×10 mL), and the collected organic layer was washed with water (30 mL) and saturated brine (30 mL), and dried over $Na_2SO_4$. After concentration by an evaporator, elution was performed with silica gel column chromatography (eluent:hexane:ethyl acetate 15:1 and 9:1) to obtain the target prostaglandin compound (10) (1.58 g, 79% yield) as a colorless oily product. δH (400 MHz; CDCl3) −0.27 (s, 3H, CH3), −0.17 (s, 3H, CH3), −0.06 (s, 3H, CH3), −0.01 (s, 3H, CH3), 0.75 (s, 9H, 3CH3), 0.82 (s, 9H, 3CH3), 1.70~1.73 (m, 2H, CH2), 2.07~2.18 (m, 4H, 2CH2), 2.25 (s, 3H, CH3), 2.35 (dd, 2H, J=7.5, 14.8 Hz, CH2), 2.54~2.73 (m, 5H, 2CH2 and CH), 3.60 (s, 3H, OCH3), 3.96~4.08 (m, 1H, CH), 5.44 (dd, 1H, J=8.0, 15.5 Hz, vinyl), 5.60 (dd, 1H, J=5.9 15.4 Hz, vinyl), 6.89-6.94 (m, 3H, aromatic), 7.06~7.10 (m, 1H, aromatic).

Example 3

In Example 3, a prostaglandin compound 12 was synthesized according to the following chemical reaction formula. Similarly to the prostaglandin compound 10, this compound can be led to 15-deoxy-16-(m-tolyl)-17,18,19,20-tetranorisocarbacyclin (15-deoxy-TIC) through an operation similar to that for the synthesis method for isocarbacyclin. This 15-deoxy-TIC is a drug discovery compound that binds to the brain prostacyclin ($IP_2$) receptor and exhibits cranial neuroprotective action. Hereinafter, the procedures for the synthesis of the compound 12 are described in detail.

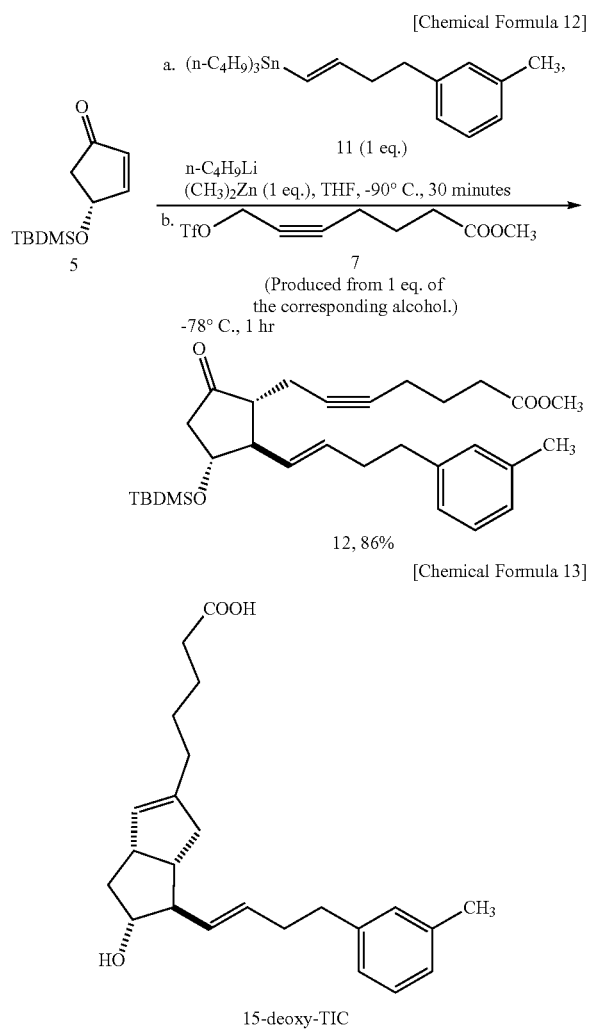

A THF solution (25 mL) of (E)-4-[(3-methyl)phenyl]-1-tributylstannyl-1-butene (11) (2.76 g, 6.34 mmol) was added to a 200-mL ampoule. After cooling to −78° C. (dry ice/acetone), n-butyllithium (1.51 M hexane solution, 4.21 mL, 6.34 mmol) was added, and the mixture was stirred at this temperature for 1 hour to adjust vinyllithium. Dimethylzinc (1.0 M hexane solution, 6.1 mL, 6.1 mmol) was added to the mixed solution. After stirring at −30° C. for 10 minutes, a flask with a corrugated tube was cooled to a temperature ranging from −98° C. to −90° C. (liquid nitrogen/methanol), and a THF solution (36 mL) of (R)-4-(tert-butyldimethylsiloxy)-2-cyclopentenone (5) (1.27 g, 6.00 mmol) was added over 2 hours using a syringe pump, and the corrugated tube was rinsed with THF (5 mL). While this mixed solution was stirred at this temperature for 30 minutes, the corresponding propargyl triflate body (7) was obtained from methyl 7-hydroxy-5-heptynoate (1.39 g, 8.93 mmol) in a similar manner as in Example 1.

A THF solution (15 mL) of the adjusted triflate 7 was added to the 200-mL ampoule tube containing the 1,4-addition reaction product at −78° C. After the mixed solution was stirred for 1 hour, the reaction was stopped with a saturated aqueous $NH_4Cl$ solution (10 mL). The resulting solution was extracted with diethyl ether (3×10 mL), and the collected organic layer was washed with water (30 mL) and saturated brine (30 mL), and dried over $Na_2SO_4$. After concentration by an evaporator, elution was performed with silica gel column chromatography (eluent:hexane:ethyl acetate 10:1) to obtain the target prostaglandin compound (12) (2.56 g, 86% yield) as a colorless oily product.

<Evaluation>

From the results of Examples 1 to 3 above, it was found that the enolate species produced by the 1,4-addition reaction with the organozinc ate complex contains dimethylzinc as a reaction residue in the reaction system, not only completely suppresses a proton exchange reaction that hinders clean alkylation, but also has sufficient reactivity with the α-side-chain triflate, and can realize a one-pot reaction of binding the three components in a stoichiometric ratio of approximately 1:1:1 without adding an additive.

In addition, when the "three-component coupling process" is performed using the unnatural ω-side chains of 15 R-TIC and 15-deoxy-TIC to synthesize a carbon skeleton, and then a bicyclic structure is constructed according to a known method for the synthesis of isocarbacyclin, a straightforward synthesis method for 15 R-TIC and 15-deoxy-TIC is completed. In the synthesis methods reported so far (conventional three-component coupling process and method via Corey lactone), 15 R-TIC: 22 steps and 15-deoxy-TIC: 26 steps, and 15 R-TIC: 27 steps and 15-deoxy-TIC: 29 steps, respectively, were needed. On the other hand, when the method of the present invention is employed, the synthesis can be performed through a very small number of steps, i.e., 9 steps.

—Methylation Reaction of Cyclopentanone Lithium Enolate (1)—

In the alkylation to the α-position after the 1,4-addition reaction of a substituent to an α,β-unsaturated ketone, it is important to prevent isomerization and byproduct formation by a hydrogen exchange reaction. In order to find out what reagents and additives can be used to suppress side reactions in the alkylation reaction after the 1,4-addition to an α,β-unsaturated ketone, tests were conducted using the methylation reaction of cyclopentanone lithium enolate (1) in THF (see the following chemical formula) as a model to examine the extent to which dimethylated products (3) and (4) were produced as byproducts, in addition to a monomethylated product (2). The details of the tests are described below.

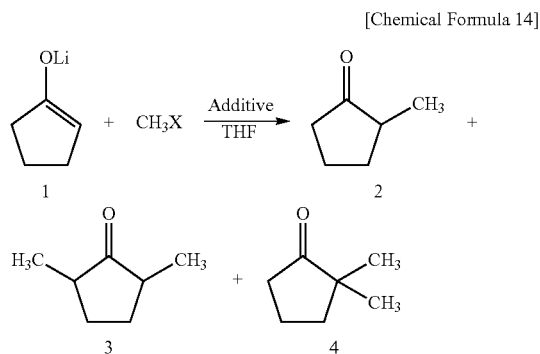

[Chemical Formula 14]

Methylation of cyclopentanone lithium enolate in THF was carried out using various methylating agents (methyl iodide in Tests 1 to 4 and methyl triflate in Tests 5 to 7) with various additives being added (see Table 1).

TABLE 1

| Ex. | CH$_3$X (Equivalent) | Additive (Equivalent) | Reaction temp. (° C.) | Reaction time (hr) | Yield(%) methyl ketone 2 | methyl ketone 3and4 |
|---|---|---|---|---|---|---|
| 1 | CH$_3$I (5) | — | −50 | 10 | 81 | 15 |
| 2 | CH$_3$I (5) | HMPA (5) | −78 | 10 | 96 | 3 |
| 3$^a$ | CH$_3$I (5) | HMPA (5) (C$_6$H$_5$)$_3$SnCl (1) | −30 | 6 | 77 | 0 |
| 4$^b$ | CH$_3$I (5) | HMPA (5) (CH$_3$)$_2$Zn (1) | −78 | 20 | 95 | 0 |
| 5$^c$ | CH$_3$OTf (1.2) | — | −78 | 1 | 98 | 2 |
| 6 | CH$_3$OTf (1.2) | (CH$_3$)$_2$Zn (1) | −78 | 2 | 100 | 0 |
| 7 | CH$_3$OTf (1.2) | (CH$_3$)$_2$Zn (3) | −78 | 2 | 100 | 0 |

$^a$Conditions of Non-Patent Document 2
$^b$Conditions of Non-Patent Document 3
$^c$Conditions of Non-Patent Document 5

As a result, when methyl iodide was used as the methylating agent, the yield of monomethyl ketone (2) was 81% even when 5 equivalents thereof were added to lithium enolate in the absence of additives. In addition, it was found that polymethylated ketones (a mixture of 3 and 4) were produced in 15% as byproducts (Test 1). In contrast, when 5 equivalents of HMPA were added as additive, the monomethyl ketone (2) was obtained in a high yield of 96%, but the polymethylated ketones (3 and 4) were also produced in 3% as byproducts (Test 2). On the other hand, it was found that, when triphenyltin chloride or dimethylzinc was added in addition to 5 equivalents of HMPA, the production of the polymethylated ketones (3 and 4) could be completely suppressed (Tests 3 and 4). However, it has been pointed out that HMPA has a carcinogenic risk for human bodies, and triphenyltin chloride also involves a problem of high toxicity to living bodies.

On the other hand, when 2 equivalents of methyl triflate (CH$_3$OTf), which was more active as a methylating agent, was added to lithium enolate, the monomethyl ketone (2) could be obtained in a high yield of 98% even in the absence of an additive, where the polymethylated ketones (3 and 4) were produced in only 2% (Test 5). Furthermore, we found, surprisingly, that when 1 equivalent or more of dimethylzinc was added as an additive, the formation of the polymethylated ketones as byproducts were completely suppressed, and only the methyl ketone (2) was quantitatively (100%) obtained without reduction in reactivity (Tests 6 and 7). Thus, it was found that the hydrogen exchange reaction leading to the production of polyalkylated ketones was completely suppressed by the coexistence of dimethylzinc, and that the enolate in the coexistence of dimethylzinc had sufficient reactivity with methyl triflate.

The present invention is not limited to the above embodiments and examples of the invention at all. Various modifications are also included in the present invention as long as they can be easily conceived by those skilled in the art without departing from the scope of the claims.

INDUSTRIAL APPLICABILITY

The 5,6-dehydro PGE$_2$ derivative (8) can be synthesized by utilizing the method for introducing substituents into an α,β-unsaturated ketone according to the present invention. This compound 8 can be extended to the synthesis of all natural prostaglandins. In addition, the selective formation of the bicyclic carbon structure with a double bond at C6-C9 positions in PG analogs comprised of additional carbon ring makes it possible to efficiently synthesize isocarbacyclin, the vertex compound of PGs with high chemical stability. Furthermore, if the side chain is converted by cleaving the w-side chain of isocarbacyclin, 15R-TIC and 15-deoxy-TIC which specifically bind to the brain IP$_2$ receptor can be synthesized, and 15S-APNIC can also be derived, which is effective for capturing and identifying the target receptor (IP') for PGI$_2$. In addition, the method can be extended to compounds other than PG-related compounds, and, in principle, can be widely used as the safe and highly-efficient carbon skeleton synthesis for useful organic compounds.

In addition, in the task of establishing methodologies capable of evaluating the function of drug transporters, which are thought to contribute to individual differences in drug efficacy and side effects, $^{11}$C-labeled compounds of 15R-TIC have been demonstrated to be effective PET probes to evaluate the transporter function involved in the biliary transport by separate evaluation of the transport ability in elementary processes involved in drug tissue transfer and excretion from quantitative analysis of the temporal transition of the drug concentration in human tissues by positron emission tomography.

The invention claimed is:

1. A method for introducing sub stituents into a carbon at an α-position and a carbon at a β-position of an α,β-unsaturated ketone, comprising:
   a first step of mixing alkyllithium and trialkylalkenyl tin in which tin binds to the vinyl position of the alkenyl group;
   a second step of mixing the mixture of the first step and dialkylzinc;
   a third step of mixing the mixture of the second step and an α,β-unsaturated ketone; and
   a fourth step of mixing the mixture of the third step and a trifluoromethanesulfonate compound, so that substituents are introduced into a carbon at an α-position and a carbon at a β-position of an α,β-unsaturated ketone.

2. A method for synthesizing a prostaglandin, comprising:
   a first step of mixing alkyllithium and trialkylalkenyl tin in which tin binds to the vinyl position of the alkenyl group;
   a second step of mixing the mixture of the first step and dialkylzinc;
   a third step of mixing the mixture of the second step and an α,β-unsaturated ketone; and
   a fourth step of mixing the mixture of the third step and a trifluoromethanesulfonate compound, so that substituents are introduced into a carbon at an α-position and a carbon at a β-position of an α,β-unsaturated ketone;
   wherein the α,β-unsaturated ketone is a γ-siloxy-cyclopentenone with a partial structure of prostaglandins; the alkenyl group of trialkylalkenyltin becomes the ω side chain of prostaglandins; the carbon chain structure of the trifluoromethanesulfonate compound becomes the α side chain of prostaglandins.

3. The method for synthesizing a prostaglandin according to claim 2, wherein in the fourth step, hexamethylphosphoric triamide (HMPA) is not present in the mixture.

* * * * *